United States Patent
Hargreaves

(10) Patent No.: US 7,576,535 B2
(45) Date of Patent: Aug. 18, 2009

(54) MULTI-COMPARTMENT SEPARATION IN MAGNETIC RESONANCE USING TRANSIENT STEADY-STATE FREE PRECESSION IMAGING

(75) Inventor: Brian A. Hargreaves, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1191 days.

(21) Appl. No.: 10/731,799

(22) Filed: Dec. 8, 2003

(65) Prior Publication Data

US 2005/0148858 A1    Jul. 7, 2005

(51) Int. Cl.
*G01V 3/00* (2006.01)
(52) U.S. Cl. ........................ 324/307; 324/309
(58) Field of Classification Search .......... 324/307, 324/309
See application file for complete search history.

(56) References Cited

U.S. PATENT DOCUMENTS

| | | | |
|---|---|---|---|
| 6,339,332 B1 * | 1/2002 | Deimling | 324/309 |
| 6,452,387 B1 * | 9/2002 | Hargreaves et al. | 324/300 |
| 2005/0085713 A1 * | 4/2005 | Reeder et al. | 600/422 |

OTHER PUBLICATIONS

Hargreaves et al. Characterization and Reduction of the Transient Response in Steady-State MR Imaging, Magn Reson Med. Jul. 2001; 46(1):149-158.*

Hargreaves, Brian A. and Nishimura, Dwight G., "*Relaxometry using Transient Steady-Sate Free Precession Imaging*", International Society for Magnetic Resonance in Medicine, 11th Annual Meeting, Poster #1100, Jul. 10, 2003, 1 page.

Harrison et al., "*Magnetization Transfer and $T_2$ Relaxation Components in Tissue*", MRM, Dec. 24, 1994, vol. 33, pp. 490-496.

Whithall, Kenneth P. and MacKay, Alexander L., "*Quantitative Interpretation of NMR Relaxation Data*", Journal of Magnetic Resonance, Nov. 22, 1988, vol. 84, pp. 134-152.

* cited by examiner

Primary Examiner—Brij B. Shrivastav
Assistant Examiner—Megann E Vaughn
(74) *Attorney, Agent, or Firm*—Beyer Law Group LLP

(57) ABSTRACT

Disclosed is a method of quantitatively separating tissue signals based on relaxation time differences. The method uses the transient signal decay in steady-state free precession (balanced SSFP) imaging to provide an alternative to standard CPMG methods of $T_2$-relaxometry. The balanced SSFP technique allows 3-4 times the temporal resolution of CPMG, and also slows the short $T_2$ decay so that it can be more accurately measured.

18 Claims, 3 Drawing Sheets

MULTI-COMPARTMENT SEPARATION IN MAGNETIC RESONANCE USING TRANSIENT STEADY-STATE FREE PRECESSION IMAGING

GOVERNMENT RIGHTS

The U.S. government has rights in the disclosed invention pursuant to NIH grants to Stanford University including NIH-HL39297, NIH-HL56394, NIH-AR46904, and NIH-CA50948.

BACKGROUND OF THE INVENTION

This invention relates generally to magnetic resonance imaging (MRI) of tissue having a plurality of tissue species with different relaxation times, and more particularly the invention relates to separation of the species from analysis of MRI relaxation curves using transient steady-state free precession (balanced SSFP) imaging.

Magnetic resonance imaging (MRI) is a widely used medical imaging modality that provides excellent soft-tissue contrast with arbitrary scan-volume orientations. Unlike X-ray computed-tomography or ultrasound, whose contrast is based only on the transmission or reflection properties of tissue, MRI generates contrast from a variety of physical properties of tissues including relaxation, chemical-shift, diffusion and proton density.

Clinically, one of the most useful MRI contrast mechanisms is $T_2$-contrast, which arises from differences in the spin-spin relaxation time ($T_2$). $T_2$-contrast has numerous uses including distinguishing malignant and benign tumors, imaging spinal abnormalities, vascular imaging and for diagnosing meniscal tears in the knee. Quantitative measurement of the $T_2$ spectrum, or $T_2$-relaxometry, is also useful for a variety of clinical applications including cartilage imaging and imaging of multiple sclerosis (MS).

$T_2$-relaxometry is discussed by Harrison et al. in "Magnetization Transfer and $T_2$-Relaxation Components in Tissue," Magnetic Resonance in Medicine 1995; 33: 490-496. Many tissues are known to exhibit multi-component $T_2$-relaxation that suggests some compartmental segregation of mobile protons on a $T_2$ time scale. Magnetization transfer (MT) is another relaxation mechanism that can be used to produce tissue contrast in MR imaging. The MT process depends strongly on water-macro molecular interactions. To investigate the relationship between multi-component $T_2$-relaxation and the MT process, multi-echo $T_2$ measurements have been combined with MT measurements. For example, in muscle, short-$T_2$ components show greater MT than long-$T_2$ components while for white matter, MT measurements were identical for two major $T_2$ components, apparently because of exchange between the $T_2$ compartments on a time scale characteristic of the MT experiment.

Whittal and Mackay, "Quantitative Interpretation of NMR Relaxation Data," Journal of Magnetic Resonance 84, 134-152 (1989), discloses a least-squares and linear programming algorithms for the interpretation of NMR relaxation data in terms of a spectrum of relaxation times.

In the case of MS, the exact $T_2$-spectrum is not as important as the fraction of the spectrum that appears in each peak. Measurement of the relative peak sizes is a good indicator of the myelination of white matter in the brain, and an indicator of MS. Currently, this measurement is performed using a multi-echo Carr-Purcell Meiboom-Gill (CPMG) sequence, see Whittal and Mackay, supra. In the CPMG sequence, the minimum echo spacing is on the order of 10-15 ms to allow for crusher gradients and 180° refocusing RF pulses.

The present invention presents a new method for quantitatively separating tissue based on relaxation time differences with shorter repetition time and improved temporal resolution.

SUMMARY OF THE INVENTION

In accordance with the invention, the exponential transient signal decay of a steady-state free precession (balanced SSFP) imaging sequence is utilized in obtaining multi-compartment separation of different tissue species, similar to the standard CPMG method of $T_2$-relaxometry. However, the short repetition time of balanced SSFP (around 3-5 ms) allows time samples on the transient curve to be 3-4 times as closely spaced as the CPMG sequences allow. Further, the exponential decay rate of balanced SSFP is slower than $T_2$ thereby allowing more time samples before the signal from short-$T_2$ species has decayed.

The invention and objects and features thereof will be more readily apparent from the following detailed description and appended claims when taken with the drawings.

DETAILED DESCRIPTION OF ILLUSTRATED EMBODIMENTS

The use of balanced SSFP imaging is advantageous compared with CPMG for short-$T_2$ species for two reasons. First, the short repetition time of balanced SSFP, around 3-5 ms allows the time samples on the exponential curve that are 3-4 times as closely spaced as the CPMG sequences allow. Second, the exponential decay rate is slower than $T_2$, allowing more time samples before the signal from short-$T_2$ species has decayed.

Standard balanced SSFP imaging consists of RF excitation pulses spaced apart by the sequence repetition time, TR. All imaging gradients are rewound, and the low spatial frequency information is acquired at an echo time (TE) midway between RF excitation pulses. A steady-state signal arises after many repetitions. The steady-state signal provides a very efficient imaging method as well as useful contrast.

In balanced SSFP imaging, magnetization gradually approaches a steady state when the signal is the same from one repetition to the next. During the time in which the steady state evolves, the transient signal can be well-predicted if the starting magnetization is known. Specifically, if the starting magnetization is roughly a scalar multiple of the steady-state magnetization, then the transient signal decays along a smooth exponential path to the steady state. The magnetization can be manipulated roughly to its steady-state direction using some smoothly increasing series of flip angles toward the flip angle of the balanced SSFP sequence. Data acquisition begins following this "catalyzation" period, as shown in FIG. 1.

Figure 1:
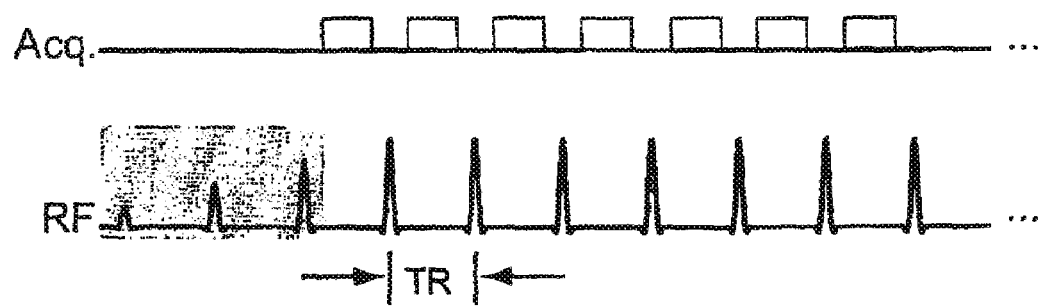
FIG. 1 illustrates a steady-state free precession imaging sequence preceded by a series of catalyzation flip pulses where acquisition begins immediately following the catalyzation period and the phase of each RF pulse alternates by 180° on each sequence repetition.

Images are acquired by repeating the sequence shown in FIG. 1 once for every phase encode line that needs to be acquired to make an image. This is similar to the $T_1$-measurement method presented by Scheffler and Hennig, "$T_1$ Quantification with Inversion Recovery TrueFISP," Magn Reson Med 2001; 45: 720-723, except that no inversion pulse is used, a larger flip angle is used, and the mixing of $T_1$ and $T_2$ is not a problem.

A sufficiently high number of sequence repetitions, such as 256, is used to sample the exponential decay long enough that the signal from voxels of interest reaches a steady state. Following this, all RF and gradient pulses are turned off for a recovery period of about one second, and then the sequence is repeated for the next phase encode line. In preliminary trials, a TR of 5 ms and a flip angle of 60° were used.

Figure 2:
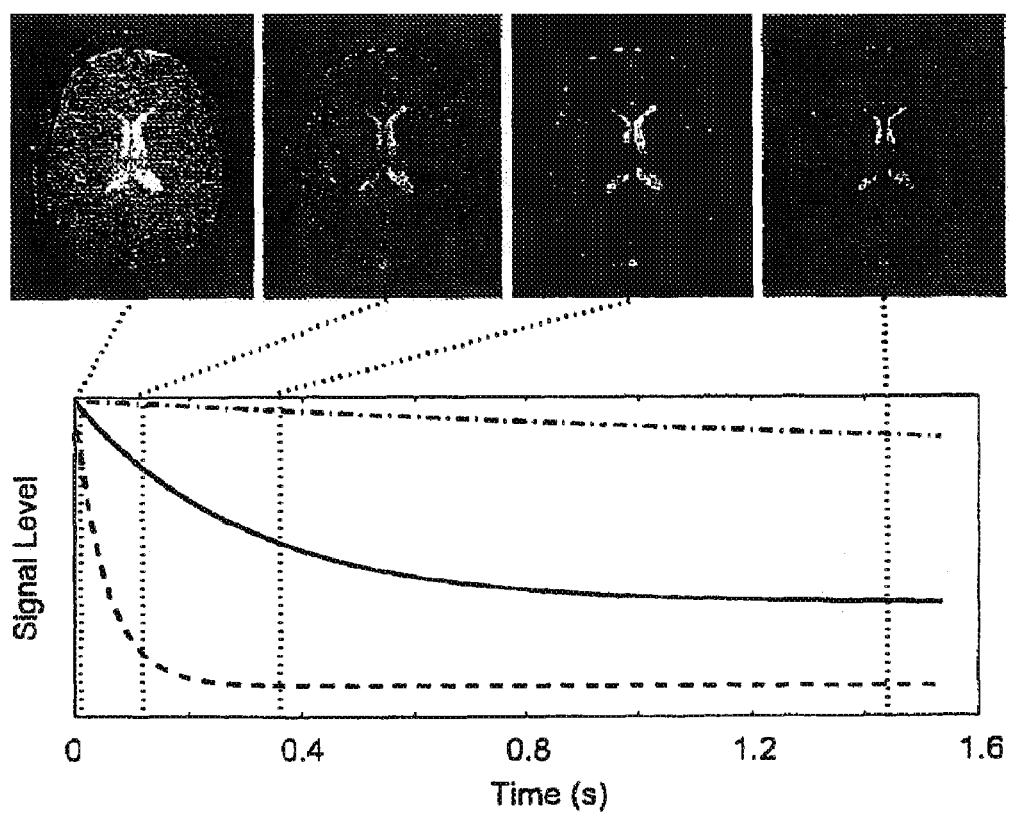
FIG. 2 illustrates brain images during a transient signal period as the steady-state magnetization evolves where the image signal is a combination of exponentially-decaying signals from cerebral-spinal fluid (dash-dot line) extracellular water in white matter (solid line) and water in myelin (dashed line).

The result of this acquisition is a series of complete images of the transient decay, spaced apart by the repetition time of the balanced SSFP sequence. A representative example is shown in FIG. 2. The figure shows the exponential responses that should arise from the short-$T_2$ myelin-water compartment, the extracellular water in white matter and the cerebral-spinal fluid (CSF). The observed signal decay in a voxel is a linear combination of decaying exponentials such as those shown.

Figure 3:
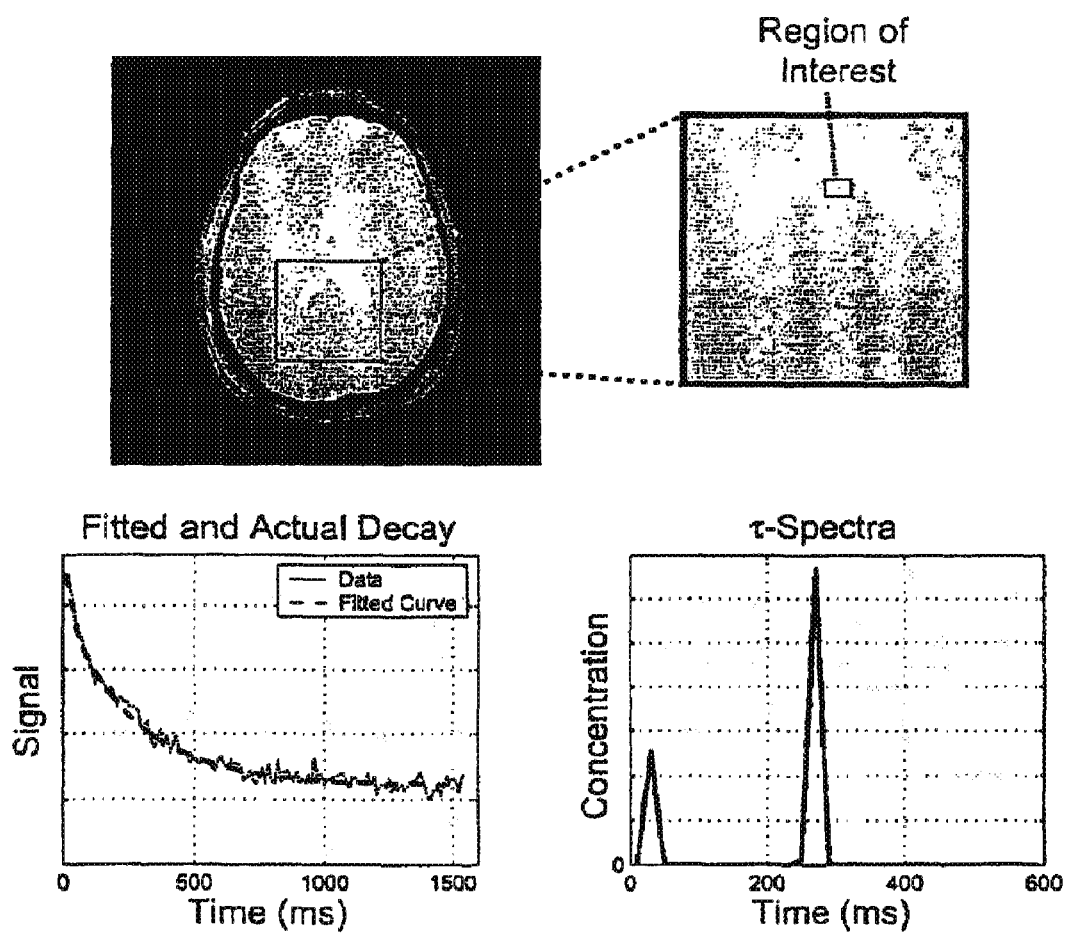
FIG. 3 illustrates τ-spectra obtained from a series of transient images shown in FIG. 2 where for a region of interest, the total signal of each image is fitted using a non-negative curve fit to determine the τ spectra and with the separate peaks in the τ spectra corresponding to myelin water and extracellular water in white matter.

A small region-of-interest (ROI) can be selected in the image, as shown in FIG. 3. The sum of all pixels in this ROI is plotted as a function of time in the bottom-left of FIG. 3. The curve was fitted to a model:

$$M(t) = \sum_{i=1}^{N} C_i e^{-\frac{t}{\tau_i}} + M_{ss} \quad (1)$$

where M(t) is the observed signal intensity as a function of time, N is the number of $\tau$ points used in the fit, $C_i$ is the relative amount of material with an exponential time constant $\tau_i$ and $M_{ss}$ is the steady-state signal in the voxel.

The coefficients $C_i$ were determined using a non-negatively constrained L1-norm method (similar to Xu et al., "Homogeneous Magnet Design Using Linear Programming," IEEE Trans Med Imaging 2000; 36: 476-483) for $\tau$ values spaced apart by 30 ms. The resulting "$\tau$-spectra" are shown in the bottom-right plot in FIG. 3. The two peaks in the $\tau$-spectra correspond to the myelin-water and extracellular water as previously reported in Mackay et al., "In vivo Visualization of Myelin Water in Brain by Magnetic Resonance," Magnetic Resonance in Medicine 1994; 31:673-677.

$T_2$-relaxometry has been performed by numerous investigators for many different purposes. The most common pulse sequences used for quantitative $T_2$ measurements are single-echo and multiple-echo (CPMG) spin-echo sequences (see Harrison et al. and Whittal and Mackay, supra). Single-echo methods are more accurate, but are very slow. CPMG methods have a minimum echo spacing of 10-15 ms depending on gradient performance and resolution. For short-$T_2$ species, this means only a few samples are obtained on the decay curve before the signal is diminished to the level of background noise.

The method in accordance with the invention has two primary advantages over CPMG techniques. First, the time samples can be spaced very closely. For image resolution of 1 mm, on current MR systems, the spacing can be as low as 3-5 ms, depending on the imaging trajectory used. For lower resolution images, the spacing could be reduced further.

The second advantage of the current method is that the decay constant $\tau$ is a combination of $T_1$ and $T_2$. When the goal of the imaging is to separate different compartments, such as myelin water and extracellular water in white matter, the mixing of $T_1$ and $T_2$ still allows separation. However, the fact that the decay constant $\tau$ is greater than $T_2$ means that the decay of short-$T_2$, species such as myelin water, is slowed. This generally reduces the error in estimating the amount of myelin water.

The combination of these two advantages means that about 10 times as many samples can be obtained on the decay curve for short-$T_2$ species such as myelin water. This can improve the reliability of the curve-fit even though the signal level is lower than in a CPMG sequence. Further, there are 2-4 more samples along the curve. Additionally, flip angle can be used to manipulate the decay rate.

The sampling method for multi-compartment analysis has been described using a simple Cartesian imaging readout and a standard balanced SSFP sequence with the catalyzation scheme described in Deimling and Heid, "Magnetization Prepared True FISP Imaging," In: Proceedings of the $2^{nd}$ Annual Meeting of SMR, San Francisco, 1994. p. 495. However, for multi-compartment analysis, the same phase-encoded frame is acquired for the entire transient decay, rather than acquiring multiple frames on one decay. The next phase-encoded frame is acquired over a subsequent transient decay. There are several variations of this method that may be useful.

First, the Cartesian imaging trajectory is slow. A spiral or echo-planar imaging trajectory can reduce the total imaging time by a factor of about 3 for balanced SSFP imaging. Alternatively, to reduce imaging time, some interleaving could be used by trading off some of the high sampling along the exponential trajectories that this method provides.

The variation of flip angle across the slice profile may cause problems. However, the effect of slice profile can be significantly reduced by using a 3D imaging trajectory. This is particularly useful in cases where signal averaging would otherwise be necessary to improve SNR.

Another variation of this sequence is to precede the magnetization preparation with an inversion pulse as described by Scheffler and Hennig, "$T_1$ Quantification with Inversion Recovery TrueFISP," Magn Reson Med 2001; 45: 720-723. This effectively changes the values of the constants C_i, increasing them in magnitude and negating them. The constrained fit would be changed accordingly to force non-positive C_i.

The invention realizes a higher achievable sampling density for relaxometry, as well as the ability to vary the decay times of different species for measurement. Particularly for short-$T_2$ materials, both of these features should improve the accuracy and the robustness of curve-fitting the exponential decays. The invention utilizes a standard balanced SSFP (FI-ESTA, TrueFISP, or balanced-FFE) imaging sequence and a preparation sequence, usually consisting of RF tips identical to those used in the balanced SSFP sequence, but of varying amplitude and/or phase and spaced apart by TR or TR/2. A sufficiently short repetition time (TR) is used such that the time constant $\tau$ does not vary much due to off resonance effects. Additionally, a curve-fitting algorithm such as non-negative least-squares (see Whittal and Mackay, supra) is used to fit multi-exponential decay.

There has been described a new method of quantitatively separating tissue based on relaxation time differences. The method uses the transient signal decay in balanced SSFP imaging to provide an alternative to the standard CPMG methods of $T_2$-relaxometry. The balanced SSFP technique allows 3-4 times the temporal resolution of CPMG, and also slows the short-$T_2$ decay so that it can be more accurately measured.

While the invention has been described with reference to specific embodiments, the description is illustrative of the invention and is not to be construed as limiting the invention. For example, a simple data frame can be acquired repeatedly over the entire decay curve of the balanced SSFP imaging sequence or multiple data frames can be acquired repeatedly over the decay curve. Further, an inversion pulse can be applied in the preparation stage whereby magnetization starts at a negative value. Alternatively, magnetization can be saturated in the preparation stage with magnetization starting at a zero value, or magnetization can be inverted in the steady state with the magnetization signal starting at a negative value. Various modifications and applications may occur to those skilled in the art without departing from the true spirit and scope of the invention as defined by the appended claims.

What is claimed is:

1. A method of separating species signals in a composite magnetic resonance imaging signal comprising the steps of:
    a) applying a series of steady-state free precession (balanced SSFP) pulse sequences, wherein evolution of the steady-state in each balanced SSFP pulse sequence follows a smooth exponential path,
    b) measuring magnetic resonance signals during transient periods for the balanced SSFP sequences as steady-state signals evolve, and
    c) fitting the transient response of the measured signals to a model to identify the smallest number of discrete exponential terms which provide a satisfactory representation of the measured data, which utilizes a curve-fitting algorithm.

2. The method as defined by claim 1 wherein the curve-fitting algorithm utilizes non-negative least-squares.

3. The method as defined by claim 2 wherein the model in step c) is defined by:

$$M(t) = \sum_{i=1}^{N} C_i e^{-\frac{t}{\tau_i}} + M_{ss}$$

where M(t) is the signal intensity as a function of time,
N is the number τ points used in the fit,
$C_i$ is relative amount of material with an exponential term constant $\tau_i$,
$M_{ss}$ is steady-state signal in a voxel, and
τ is the exponential term in the fitting model.

4. The method as defined by claim 2 wherein a single data frame is acquired repeatedly over decay of the magnetic resonance signals.

5. The method as defined by claim 4 wherein before step a) a plurality of preparation pulses are applied, wherein an inversion pulse is applied with the preparation pulses and magnetization starts at a negative value.

6. The method as defined by claim 4 wherein before step a) a plurality of preparation pulses are applied and magnetization is saturated thereby.

7. The method as defined by claim 4 wherein before step a) a plurality of preparation pulses are applied and magnetization starts in a steady state and is inverted in the steady state.

8. The method as defined by claim 2 wherein multiple data frames are acquired repeatedly over decay of the magnetic resonance signals.

9. The method as defined by claim 8 wherein before step a) a plurality of preparation pulses are applied, wherein an inversion pulse is applied with the preparation pulses and magnetization starts at a negative value.

10. The method as defined by claim 8 wherein before step a) a plurality of preparation pulses are applied and magnetization is saturated thereby.

11. The method as defined by claim 8 wherein before step a) a plurality of preparation pulses are applied and magnetization starts in a steady state and is inverted in the steady state.

12. The method as defined by claim 2 wherein before step a) a plurality of preparation pulses are applied, wherein an inversion pulse is applied with the preparation pulses and magnetization starts at a negative value.

13. The method as defined by claim 2 wherein before step a) a plurality of preparation pulses are applied and magnetization is saturated thereby.

14. The method as defined by claim 2 wherein before step a) a plurality of preparation pulses are applied and magnetization starts in a steady state and is inverted in the steady state.

15. The method as defined by claim 1 wherein the model in step c) is defined by:

$$M(t) = \sum_{i=1}^{M} C_i e^{\frac{t}{\tau_i}} + M_{ss}$$

where M(t) is the signal intensity as a function of time,
N is the number τ points used in the fit,
$C_i$ is relative amount of material with an exponential term constant $\tau_i$,
$M_{ss}$ is steady-state signal in a voxel, and
τ is the exponential term in the fitting model.

16. The method as defined by claim 1 wherein before step a) a plurality of preparation pulses are applied, wherein an inversion pulse is applied with the preparation pulses and magnetization staffs at a negative value.

17. The method as defined by claim 1 wherein before step a) a plurality of preparation pulses are applied and magnetization is saturated thereby.

18. The method as defined by claim 1 wherein before step a) a plurality of preparation pulses are applied and magnetization staffs in a steady state and is inverted in the steady state.

* * * * *

UNITED STATES PATENT AND TRADEMARK OFFICE
CERTIFICATE OF CORRECTION

PATENT NO. : 7,576,535 B2  Page 1 of 1
APPLICATION NO. : 10/731799
DATED : August 18, 2009
INVENTOR(S) : Brian A. Hargreaves It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1608 days.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,576,535 B2  
APPLICATION NO. : 10/731799  
DATED : August 18, 2009  
INVENTOR(S) : Hargreaves et al.

Page 1 of 1

It is certified that error appears in the above-identified patent and that said Letters Patent is hereby corrected as shown below:

In the Specification Under Column 1:

• Please replace Column 1, line no. 6-11 with:

-- FEDERALLY-SPONSORED RESEARCH OR DEVELOPMENT  
This invention was made with Government support under contracts HL039297, HL056394, AR046904, and CA050948 awarded by the National Institutes of Health. The Government has certain rights in this invention. --

Signed and Sealed this
Twenty-third Day of April, 2013

Teresa Stanek Rea
*Acting Director of the United States Patent and Trademark Office*